US00PP29736P3

(12) United States Plant Patent
Braeunig

(10) Patent No.: US PP29,736 P3
(45) Date of Patent: Oct. 9, 2018

(54) ***LEUCANTHEMUM* PLANT NAMED 'FLORLEULAG'**

(50) Latin Name: *Leucanthemum x superbum*
Varietal Denomination: Florleulag

(71) Applicant: Florensis B.V., Hendrik-Ido-Ambacht (NL)

(72) Inventor: Tobias M. Braeunig, Quedlinburg (DE)

(73) Assignee: Florensis B.V., Hendrik-Ido-Ambacht (NL)

( * ) Notice: Subject to any disclaimer, the term of this patent is extended or adjusted under 35 U.S.C. 154(b) by 0 days.

(21) Appl. No.: 15/731,892

(22) Filed: Aug. 21, 2017

(65) Prior Publication Data

US 2018/0168084 P1 Jun. 14, 2018

Related U.S. Application Data

(60) Provisional application No. 62/498,061, filed on Dec. 12, 2016.

(51) Int. Cl.
*A01H 5/02* (2018.01)

(52) U.S. Cl.
USPC ..... Plt./285
CPC ..... *A01H 5/02* (2013.01)

(58) Field of Classification Search
USPC ..... Plt./285
See application file for complete search history.

*Primary Examiner* — Susan McCormick Ewoldt
(74) *Attorney, Agent, or Firm* — Audrey Charles

(57) ABSTRACT

A new and distinct cultivar of *Leucanthemum* plant named 'Florleulag', characterized by its white-colored inflorescences, medium green-colored foliage, and moderately vigorous, compact-upright growth habit, is disclosed.

1 Drawing Sheet

Latin name of genus and species of plant claimed: *Leucanthemum* x *superbum.*

Variety denomination: 'Florleulag'.

BACKGROUND OF THE INVENTION

The present invention relates to a new and distinct cultivar of *Leucanthemum* plant botanically known as *Leucanthemum* x *superbum* and hereinafter referred to by the cultivar name 'Florleulag'.

The new cultivar originated in a controlled breeding program in Quedlinburg, Germany during July 2011. The objective of the breeding program was the development of *Leucanthemum* cultivars having large inflorescences with early seasonal flowering.

The new *Leucanthemum* cultivar is the result of open-pollination. The female (seed) parent of the new cultivar is the proprietary *Leucanthemum* x *superbum* breeding selection coded 180-1, not patented, characterized by its white-colored flowers, medium green-colored foliage, and vigorous, upright growth habit. The male (pollen) parent of the new cultivar is unknown. The new cultivar was discovered and selected as a single flowering plant within the progeny of the above stated open-pollination during August 2012 in a controlled environment in Quedlinburg, Germany.

Asexual reproduction of the new cultivar by terminal stem cuttings since August 2012 in Quedlinburg, Germany and Elburn, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Florleulag' as a new and distinct cultivar of *Leucanthemum* plant:

1. White-colored inflorescences;
2. Medium green-colored foliage; and
3. Moderately vigorous, compact-upright growth habit.

Plants of the new cultivar differ from plants of the female parent primarily in having lower growth vigor, larger-sized flowers with earlier seasonal flowering.

Of the many commercially available *Leucanthemum* cultivars, the most similar in comparison to the new cultivar is the *Leucanthemum* cultivar 'Snowcap', not patented. However, in side by side comparisons, plants of the new cultivar differ from plants of 'Snowcap' in at least the following characteristics:

1. Plants of the new cultivar have larger diameter inflorescences than plants of 'Snowcap'; and
2. Plants of the new cultivar have earlier seasonal flowering than plants of 'Snowcap'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Florleulag'. The plants were approximately 15 weeks old and were grown in 13 cm pots for approximately 10 weeks in a glass-covered greenhouse in Hendrik-Ido-Ambacht, The Netherlands.

DETAILED BOTANICAL DESCRIPTION

Figure 1:
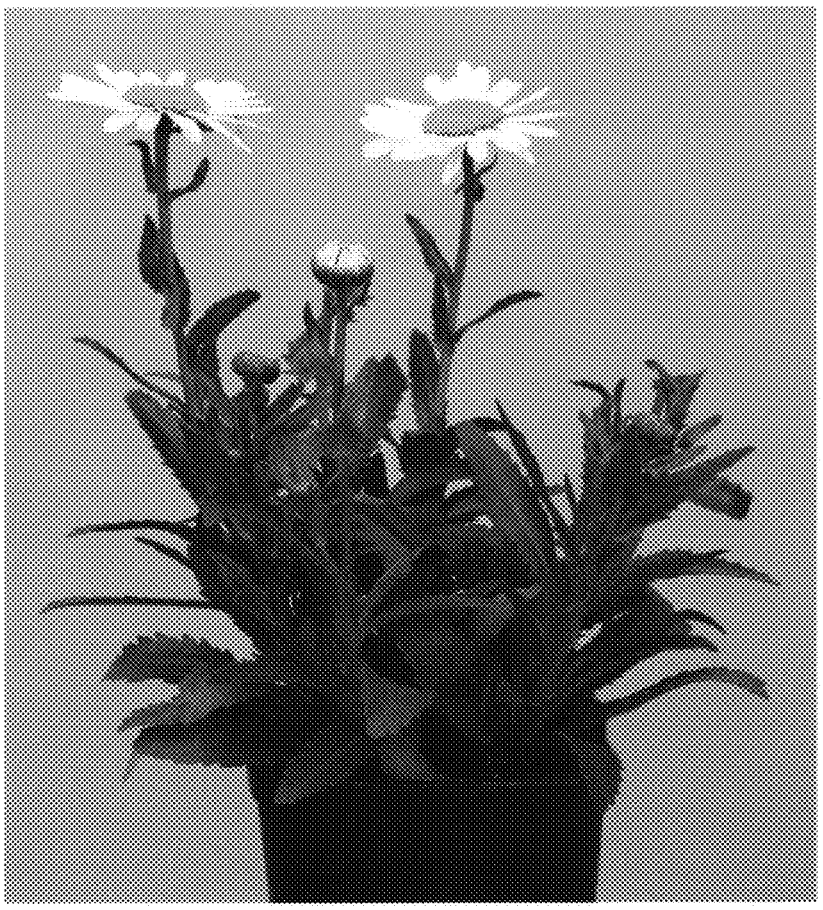
FIG. 1 illustrates a side view of the overall growth and flowering habit of 'Florleulag'.
Figure 2:
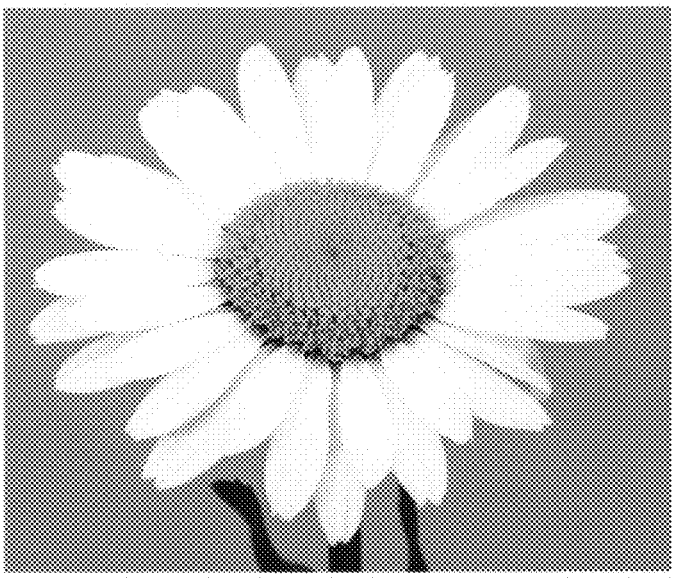
FIG. 2 illustrates a close-up view of an individual inflorescence of 'Florleulag'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in June 2017 under natural light conditions in Boskoop, The Netherlands.

The following descriptions and measurements describe approximately 15 week old plants produced from cuttings from stock plants and grown in a glass-covered greenhouse in Hendrik-Ido-Ambacht, The Netherlands under conditions comparable to those used in commercial practice. The plants were grown in 13 cm pots utilizing a soilless growth medium for approximately 10 weeks. During this period the temperatures ranged from 57.2° F. to 64.4° F. (14.0° C. to 18.0° C.). No supplemental lighting was provided. Measurements and numerical values represent averages of typical plants.

Botanical classification: *Leucanthemum* x *superbum* 'Florleulag'.

Parentage:

*Female parent*.—Proprietary *Leucanthemum* x *superbum* breeding selection coded 180-1, not patented.

*Male parent*.—Unknown.

Propagation:

*Type cutting*.—Terminal stem.

*Time to initiate roots*.—Approximately 10 to 12 days at 70° F. (21° C.).

*Time to produce a rooted cutting*.—Approximately 5 to 6 weeks at 70° F. (21° C.).

*Root description*.—Fibrous, thin, white in color.

*Rooting habit*.—Freely branching, dense.

Plant description:

*Commercial crop time*.—Approximately 10 to 12 weeks from a rooted cutting to finish in a one-gallon container.

*Growth habit and general appearance*.—Moderately vigorous, compact-upright growth habit.

*Plant type*.—Herbaceous perennial.

*Hardiness*.—USDA zones 4a to 9b.

*Size*.—Height from soil level to top of plant plane: Approximately 21.8 cm. Width: Approximately 23.6 cm.

*Branching habit*.—Freely branching, pinching improves basal branching. Quantity of lateral branches per plant: Approximately 7.

*Lateral branch*.—Strength: Strong. Length: Approximately 6.0 cm. Diameter: Approximately 4.0 mm. Length of central internode: Approximately 1.0 cm. Texture: Slightly glossy, glabrous. Color of young stems: 143C. Color of mature stems: 137C.

Foliage description:

*General description*.—Quantity of leaves per lateral branch: Approximately 15. Fragrance: None detected. Form: Single. Arrangement: Alternate.

*Leaves*.—Aspect: Acute angle to stem; perpendicular to obtuse angle to stem with age. Shape: Lanceolate. Margin: Coarsely serrate. Apex: Bluntly acute. Base: Sessile, truncate. Venation pattern: Pinnate. Length of mature leaf: Approximately 7.5 cm. Width of mature leaf: 2.1 cm. Texture of upper surface: Very slightly glossy, glabrous. Texture of lower surface: Very slightly glossy, glabrous. Color of upper surfaces of young foliage: 137B with midvein of 144C. Color of lower surfaces of young foliage: 137C with midvein of 144C. Color of upper surfaces of mature foliage: NN137A with main venation of 144A and 144B. Color of lower surfaces of mature foliage: in between 137B and 138A with main venation of 143B.

Flowering description:

*Flowering habit*.—'Florleulag' is freely flowering under outdoor growing conditions with substantially continuous blooming from early to late summer.

*Lastingness of individual inflorescence on the plant*.—Approximately 14 days.

Inflorescence description:

*General description*.—Type: Daisy-type composite, actinomorphic. Persistent. Shape: Round. Aspect: Erect. Arrangement: Terminal capitulum, positioned above and below the foliage. Quantity per plant: Approximately 3. Diameter: Approximately 7.3 cm. Depth: Approximately 1.7 cm. Fragrance: None detected.

*Peduncle*.—Strength: Strong. Aspect: Erect. Length: Approximately 8.4 cm. Diameter: Approximately 3.5 mm. Texture: Glabrous, slightly glossy. Color: 137C.

*Bud*.—Rate of opening: Generally takes 4 to 5 days for bud to progress from first color to fully open inflorescence. Quantity per plant: Approximately 17.

*Bud just before opening*.—Shape: Oblate. Diameter: Approximately 1.8 cm. Depth: Approximately 1.4 cm. Color: Slightly lighter than 150D.

*Ray florets*.—Quantity per inflorescence: Approximately 36. Arrangement: In a single whorl, imbricate. Aspect: Slightly concave. Shape: Elliptic. Margin: Entire. Apex: Three acute tips. Base: Cuneate. Length: Approximately 2.8 cm. Width: Approximately 7.0 mm. Texture of upper and lower surfaces: Glabrous, axially ribbed. Color of upper and lower surfaces when first open: NN155B. Color of upper and lower surfaces when fully open: NN155D.

*Disc florets*.—Quantity per inflorescence: Approximately 400. Arrangement: Massed in center of inflorescence. Shape: Tubular, lower 90% fused. Margin: Entire. Apex: Five acute tips. Base: Fused. Length: Approximately 7.5 mm. Diameter: Approximately 2.0 mm. Texture of outer surface: Slightly glossy, glabrous. Texture of inner surface: Glandular pubescent on tips. Color of upper or inner surface when first and fully open: 144B with tips of 9A and base of 145B. Color of lower or outer surface when fully open: 144B with tips of 9A and base of 145B.

*Disc*.—Diameter: Approximately 2.7 cm. Depth: Approximately 7.0 mm.

*Receptacle*.—Shape: Cone. Height: Approximately 4.0 mm. Diameter at base: Approximately 1.1 cm. Color: 145A to 145B.

*Phyllaries*.—Quantity per inflorescence Approximately 75. Arrangement: In three equally divided whorls. All bracts unfused, inner bracts surround receptacle, slightly imbricate, held close to ray florets.

*Outer phyllaries*.—Shape: Ovate. Margin: Entire. Apex: Bluntly acute. Base: Truncate. Length: Approximately 7.0 mm. Width: Approximately 3.0 mm. Texture of upper surfaces: Glabrous, glossy.

Texture of lower surfaces: Glabrous, matte. Color of upper and lower surfaces: 143A.

*Inner phyllaries*.—Shape: Ovate. Margin: Entire. Apex: Bluntly acute. Base: Truncate. Length: Approximately 9.0 mm. Width: Approximately 4.0 mm. Texture of upper surfaces: Glabrous, glossy. Texture of lower surfaces: Glabrous, matte. Color of upper and lower surfaces: 143A with margins transparent 199D.

*Reproductive organs*.—Androecium: Present on disc florets only. Stamen quantity: 5. Stamen length: Approximately 4.0 mm. Filament length: Approximately 2.0 mm. Filament color: NN155D. Anther shape: Oblong, basifixed. Anther length: Approximately 2.0 mm. Anther color: 13A to 13B. Pollen amount: Moderate to abundant. Pollen color: 23A. Gynoecium: Present on ray and disc florets. Pistil quantity: 1 per floret. Pistil length: Approximately 6.0 mm. Stigma shape: Bifid. Stigma length: Approximately 1.0 mm. Stigma color: 9B. Style length: Approximately 5.0 mm. Style color: 145C. Ovary length: Approximately 1.5 mm. Ovary color: 145B.

Seed and fruit production: Neither seed nor fruit production has been observed.

Disease and pest resistance: Resistance to pathogens and pests common to *Leucanthemum* has not been observed.

What is claimed is:

1. A new and distinct cultivar of *Leucanthemum* plant named 'Florleulag', substantially as herein illustrated and described.

* * * * *